United States Patent [19]

DeHaan et al.

[11] Patent Number: 4,649,937
[45] Date of Patent: Mar. 17, 1987

[54] ETCHED GROOVED ELECTRODE FOR PACING LEAD AND METHOD FOR MAKING SAME

[75] Inventors: Abel DeHaan; W. Kinzy Jones, both of Pembroke Pines; Richard D. Krug, Miami, all of Fla.

[73] Assignee: Cordis Corporation, Miami, Fla.

[21] Appl. No.: 695,708

[22] Filed: Jan. 28, 1985

[51] Int. Cl.⁴ .............................................. A61N 1/04
[52] U.S. Cl. .................................. 128/784; 128/419 P
[58] Field of Search .................... 128/642, 419 P, 784, 128/785, 786

[56] References Cited

U.S. PATENT DOCUMENTS

| | | | |
|---|---|---|---|
| 3,911,928 | 10/1975 | Lagergren | 128/419 P |
| 4,011,861 | 3/1977 | Enger | 128/419 P |
| 4,033,357 | 7/1977 | Helland et al. | 128/785 |
| 4,280,514 | 7/1981 | MacGregor | 128/786 |
| 4,352,360 | 10/1982 | King | 128/786 |
| 4,407,302 | 10/1983 | Hirshorn et al. | 128/784 |
| 4,408,604 | 10/1983 | Hirshorn et al. | 128/785 |
| 4,440,178 | 4/1984 | Bussard et al. | 128/784 |
| 4,502,492 | 3/1985 | Bornzin | 128/786 |

OTHER PUBLICATIONS

Kuperstein et al., "I.E.E.E. Transactions on Biomedical Engineering", V. BME-28, No. 3, Mar. 1981, pp. 288-293.

Primary Examiner—William E. Kamm
Attorney, Agent, or Firm—Henry W. Collins; Thomas R. Vigil

[57] ABSTRACT

The tip electrode member has a rounded or bullet shaped distal end and has grooves etched into the distal end to increase the surface area of the electrode member within a small displaced surface area to minimize polarization of the tip electrode member while ensuring sufficient electric current flow to cause heart muscle depolarization. Preferably, the tip electrode member is made of titanium or a titanium alloy and is coated with carbon.

22 Claims, 3 Drawing Figures

ETCHED GROOVED ELECTRODE FOR PACING LEAD AND METHOD FOR MAKING SAME

BACKGROUND OF THE INVENTION

1. Field of the Invention

The present invention relates to a method for making an implantable pacing lead tip electrode for use with a pacing lead assembly. The tip electrode is formed from an electrically conductive material and with a plurality of grooves or recesses which are etched into the tip electrode circumferentially and parallel to the horizontal and vertical transverse axes of the tip electrode to provide a large surface area within a small displaced surface area on the tip electrode to minimize electrode polarization while providing sufficient current flow for heart muscle depolarization.

2. Description of the Prior Art

Heretofore, various tip electrodes have been proposed having porous surfaces or other surfaces for increasing the surface area of the tip electrode. Examples of such previously proposed electrodes are disclosed in various prior U.S. patents.

For example, the Enger U.S. Pat. No. 4,011,861 discloses an implantable electric terminal for organic tissue which is porous and intermeshes with the tissue. The electric terminal is composed of a tissue-compatible implantable material which is electrically conductive, such as platinum or an alloy, and which has on at least one surface thereof a porous material or layer having pores that are interconnected and continuous so that body electrolytes and/or tissue containing blood capillaries can contact the electrically conductive material through the porous material or layer.

The MacGregor U.S. Pat. No. 4,280,514 discloses an endocardial pacemaker electrode having a dense rigid metal substrate and a rigid porous metal coating which adheres to at least a major portion of the substrate. The porous coating includes a plurality of metal particles bonded together at their points of contact with each other and with the substrate to form a network of interconnected pores substantially uniformly distributed throughout the coating.

The King U.S. Pat. No. 4,352,360 discloses a semiconductor low-threshold electrode having a plurality of materials which are arranged in layers such that the material having the lowest conductivity is in direct contact with body tissue.

The Hirshorn et al U.S. Pat. No. 4,407,302 discloses a cardiac pacemaker electrode tip structure having an electrode tip having an external surface with a concave region formed thereon to increase the pacing impedance thereof. The external surface of the electrode tip is roughened to increase the microsurface area of the electrode tip and to reduce the sensing impedance thereof.

The Hirshorn et al U.S. Pat. No. 4,408,604 discloses a porous pacemaker electrode tip comprising a concavo-convex electrode cap having a plurality of apertures therethrough and an electrode shaft having a supporting edge formed thereon to which the concave surface of the electrode is joined. The porous cardiac pacemaker electrode is formed by deforming a platinum plate into a concave-convex shaped cap member, thereby forming a plurality of selectively spaced apertures through the electrode cap member to make the electrode cap substantially porous.

The Bussard et al U.S. Pat. No. 4,440,178 discloses an implantable electrode which is porous and includes a sintered member made of electrically conductive particles. The particles are covered with a material of lower electrical conductivity than that of the particles, the particles being metals selected from the group comprising tantalum, titanium, molybdenum, zirconium or cobalt-chromium based alloys.

As will be described in greater detail hereinafter, the tip electrode and the method of making same of the present invention differ from the various tip electrodes previously proposed by providing a tip electrode having a plurality of grooves etched into the surface of the tip electrode to provide a large surface area to minimize polarization of the electrode while at the same time, keeping the same overall outer diameter of the electrode so that the large surface area is within a small displaced surface area to ensure an electric current flow sufficient to cause muscle depolarization of the heart. Since the grooves are etched into the surface of the tip electrode, the pattern of and the number of grooves can be controlled and can be easily changed.

SUMMARY OF THE INVENTION

According to the invention there is provided a method for making an implantable tip electrode member for use with a pacing lead. The method includes the steps of: forming a tip electrode member from an electrically conductive material, the member having a proximal end and a round-in-cross-section distal end; coating the distal end with a photosensitive material; directing a light source against the distal end through a template having light passages therein permitting passage of light therethrough, to create a pattern of light-exposed areas and a pattern of non-exposed or dark areas between the light-exposed areas on the distal end, the photosensitive material on the light-exposed areas being polymerized to an insoluble state thereby forming a protective coating on the light-exposed areas; applying a first solvent to the tip electrode member, the first solvent removing the photosensitive material from the non-exposed areas of said tip member thereby leaving a pattern of light-exposed areas having the photosensitive material adhered thereto; applying an etchant to the tip electrode member to etch a plurality of grooves in the non-exposed areas with the light-exposed areas being protected by the photosensitive material to form a plurality of ridges between the grooves; arranging and locating the light passages so that the plurality of grooves includes a first set of grooves comprising at least two grooves extending circumferentially around the generally round-in-cross-section distal end in generally parallel spaced planes and a second set of grooves comprising at least two grooves extending over the round-in-cross-section distal end in planes perpendicular to the planes of the first set of grooves; and applying a second solvent to the tip electrode member to remove the photo-sensitive material from the light-exposed areas.

Further according to the invention there is provided an implantable tip electrode member made of an electrically conductive material and having a proximal end and a generally hemispherically shaped distal end. The generally hemispherically shaped distal end of the tip electrode member has a plurality of grooves in the surface thereof forming a plurality of ridges between the grooves to provide a large surface area within a small displaced surface area. The grooves include a first set of grooves comprising at least two grooves extending circumferentially around the generally hemispherically shaped distal end in generally parallel spaced planes, and a second set of grooves comprising at least two grooves extending over the hemispherically shaped distal end in planes which are perpendicular to the planes of the first set of grooves. It is believed that this construction and arrangement of grooves minimizes polymerization of the tip electrode member while ensuring sufficient current flow to cause heart muscle depolarization.

DESCRIPTION OF THE PREFERRED EMBODIMENT

Figure 1:
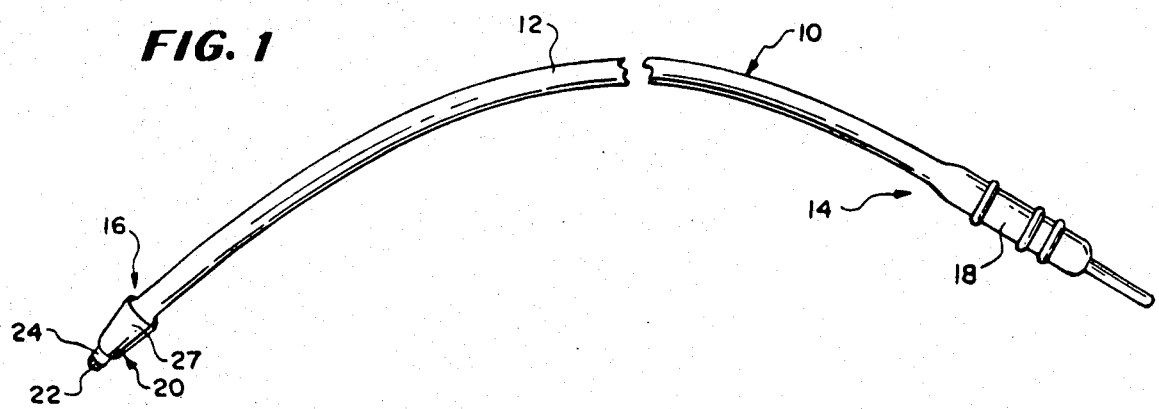
FIG. 1 is a perspective view of a pervenous pacing lead assembly, with a portion broken away, having an implantable tip electrode member constructed according to the teachings of the present invention electrically connected at the distal end thereof.

Referring now to FIG. 1, there is illustrated therein a pervenous pacing lead assembly 10 comprising a conductive lead 12 having a proximal end 14 and a distal end 16, a terminal plug assembly 18 electrically connected to the proximal end 14, and an implantable tip electrode member 20 electrically connected to the distal end 16 of the conductive lead 12 and constructed according to the teachings of the present invention.

The pervenous pacing lead assembly 10, to which the tip electrode member 20 is connected, is introduced into an appropriate vein of a body and advanced to the right ventricle of the heart of the body where the tip electrode member 20 is placed into position. As will be described in greater detail hereinafter, the tip electrode member 20 includes an outer surface 22 which provides an increased surface area within a small displaced surface area of the electrode 20 to minimize electrode polarization while ensuring sufficient current flow for heart muscle depolariation.

The plug assembly 18 electrically connected to the proximal end 14 of the conductive lead member 12 is adapted to be plugged into a plug receiving socket (not shown) of an implantable cardiac pacer (not shown). Electrical impulses produced by the cardiac pacer are conducted from the plug assembly 18 through the conductive lead 12 to the tip electrode member 20 which is in direct electrical contact with the tissue of the heart in order to stimulate and/or defibrillate the muscles of the heart into which the tip electrode member 20 has been implanted.

Figure 2:
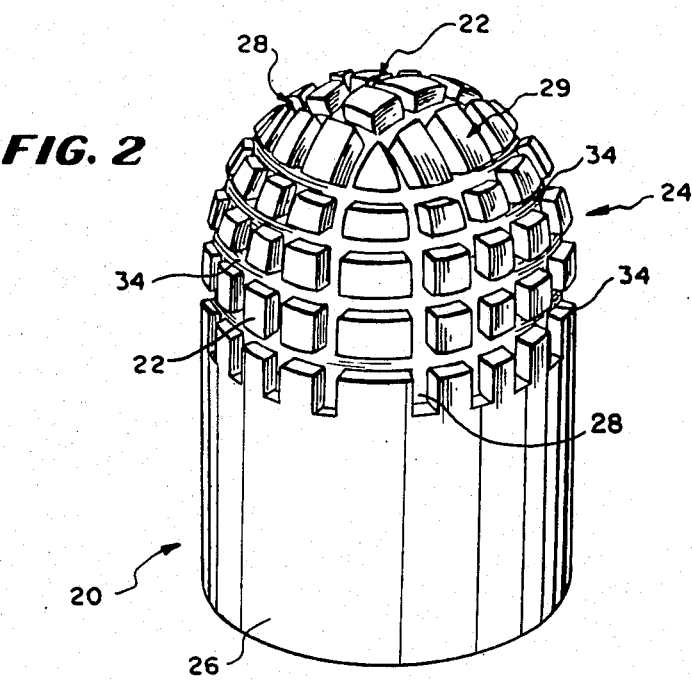
FIG. 2 is an enlarged perspective view of the implantable tip electrode member of the present invention.

Referring now to FIG. 2, the tip electrode member 20 comprises a distal end 24 and a proximal end 26 electrically connected to the distal end 16 of the conductive lead member 12. As shown in FIG. 1, the proximal end 26 of the tip electrode member 20 is surrounded by an insulative member 27 having a conical configuration to permit the pervenous pacing lead assembly 10 to be easily maneuvered through a vein of a body.

The distal end 24 of the electrode member 20 is bullet shaped or round-in-cross-section and is made of an electrically conductive material, preferably titanium or a titanium alloy comprising 90% titanium, 6% aluminum, and 4% vanadium.

According to the teachings of the present invention, the distal end 24 of the tip electrode member 20 is formed with a plurality of grooves 28 which establish ridges 29 therebetween to increase the surface area of the distal end 24 of the tip electrode member 20 in order to minimize electrode polarization of the tip electrode member 20, while at the same time, keeping the overall outer diameter of the electrode tip member 20 the same so that the large surface area is within a small displaced surface area to ensure sufficient electric current flow to cause muscle depolarization of the heart.

The grooves 28 are etched into the surface 22 of the distal end 24 of the electrode tip member 20 such as by chemical, electrochemical or plasma etching. In one preferred embodiment the etching is accomplished by first applying a thin coat of a photosensitive material, preferably a photosensitive polymeric material.

After the thin coat of the photosensitive material has dried, a light source is directed against the distal end 24 of the tip electrode member 20 through a mask or template (not shown) having a plurality of transparent windows. The light which passes through the windows in the template establishes a pattern or array of light-exposed areas on the distal end 24 of the tip electrode member 20 having dimensions approximately equal to the dimensions of the windows in the template. Accordingly, a pattern of light-exposed areas corresponding to the ridges 29, and a pattern of nonexposed or dark areas between the light-exposed areas corresponding to the grooves 28, are established on the distal end 24 of the tip electrode member 20. The photosensitive material on the distal end 24 of the tip electrode member 20 which is exposed to light polymerizes and becomes insoluble.

The template is preferably made of a plastic material, such as a plastic material sold under the trademark MYLAR, and is generally opaque except for the plurality of the transparent windows in the template. The windows are preferably elongate slots having dimensions approximately equal to the desired dimensions of the ridges 29, and are equal in number to the desired number of ridges 29. Circular transparent windows instead of elongate slots also can be used. Similarly, the opaque areas between the transparent windows have dimensions approximately equal to the desired dimensions of the grooves 28. In this respect, the template is either in the form of a flat, circular, planar mask, or preferably, a concave circular mask which is conformal to the round in cross-section distal end 24 of the electrode tip member 20 and is provided with a plurality of windows so that the distal end 24 of the tip electrode member 20 has corresponding light-exposed areas directed thereon and around the circumference thereof. The windows are preferably arranged so that four elongate windows are parallel relative to each other and perpendicular to another four elongate windows which are also parallel to each other. The template is further provided with four circular windows which are spaced from each other and arranged parallel relative to each other and circumferentially around the template.

Figure 3:
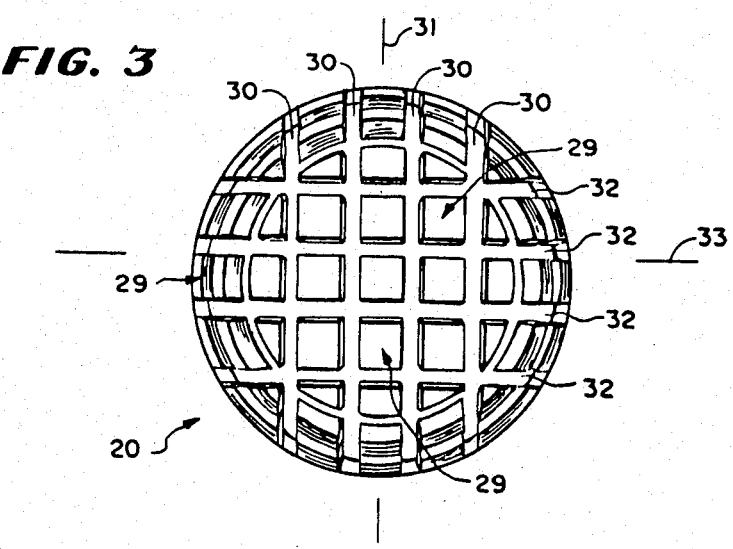
FIG. 3 is a top view of the tip electrode member shown in FIG. 2.

As a result and as shown in FIG. 3, the grooves 28 in the distal end 24 of the electrode tip member 20 include four grooves 30 which extend across (and around—FIG. 2) the distal end 24 of the tip electrode member 20 in a direction parallel to a transverse vertical axis 31 of the tip electrode member 20 and four grooves 32 which extend across (and around—FIG. 2) in a direction parallel to a transverse horizontal axis 33 of the electrode member 20. Also, as shown in FIG. 2 and partially in FIG. 3, four grooves 34 extend circumferentially around the distal end 24 of the tip electrode member 20 and in a direction normal to the elongate axis of the tip electrode member 20, with the ridges 29 therebetween.

After the distal end 24 of the tip electrode member 20 has been exposed to the light source and the photosensitive material has been caused to polymerize and thus rendered insoluble, a suitable first solvent is applied to the tip electrode member 20 which effectively removes the photosensitive material from the dark, nonexposed and nonbound areas of the tip electrode member 20 between the light exposed areas. Once the photosensitive material has been removed from the dark, nonexposed areas, an adherent pattern of the molecularly bound photosensitive material in the shape of the elongate window areas of the template remains on the distal end 24 of the tip electrode member 20.

According to the teachings of the present invention, the grooves 28, which comprise the grooves 30, 32 and 34, are etched into the surface 22 of the distal end 24 of the electrode tip member 20 thereby forming ridges 29 therebetween. The grooves 28 are etched into the surface 22 of the tip electrode member 20 by applying an appropriate solvent or etchant to the tip electrode member 20 which is chemically reactive with the titanium material or titanium alloy material from which the tip electrode member 20 is made. The etchant is chemically nonreactive with the photosensitive material which coats the tip electrode member 20, and is chemically reactive with the titanium or titanium alloy material from which the tip electrode member 20 is made. In this manner, the protected light-exposed areas of the tip electrode member 20 having the photosensitive material bound thereto are unaffected by the etchant to thereby protect the underlying titanium or titanium alloy material, and the etchant chemically reacts with the unprotected titanium or titanium alloy material which is thereby eroded to a desired depth so as to etch the grooves 28 comprising grooves 30, 32 and 34 into the electrode member 20 and forming the ridges 29 therebetween.

Accordingly, and referring again to FIGS. 2 and 3, the grooves 28 are photochemically etched into the surface 22 of the distal end 24 of the electrode member 20 thereby forming the ridges 29 therebetween, the grooves 28 and ridges 29 extending over and circumferentially around the distal end 24 of the tip electrode member 20.

The dimensions of the grooves 28 and the ridges 29 may vary, although preferably, the grooves 28 are approximately 0.002 inch wide and approximately 0.002 inch deep and similarly, the ridges 29 are 0.002 inch wide and approximately 0.002 inch high, in order to establish a large surface area.

The increased surface area created on the sides of the ridges 29 in the grooves 28 make greater electrical contact with the organ tissue with a small displaced surface area to provide sufficient electric current flow to ensure effective heart muscle depolarization and at the same time minimize polarization of the tip electrode member 20.

After the grooves 28 and the ridges 29 have been formed to their desired dimensions as heretofore described, the titanium/titanium alloy etchant is removed with an appropriate solvent so that the surface 22 of the electrode member 20 does not have any material adhered thereto that would interfere with its electrical conductivity.

Since the titanium/titanium alloy material from which the distal end 24 of the tip electrode member 20 is made in a soft metal, preferably the distal end 24 of the electrode tip member 20 is coated with an electrically conductive material, such as carbon, after the grooves 28 have been etched into the distal end 24 of the electrode member 20 and the ridges 29 formed therebetween.

The carbon coating is deposited onto the surface 22 of the electrode member 20 from a glow discharge plasma of a hydrocarbon containing gas. The electrode member 20 is first glow discharge plasma etched using a plasma that will remove the oxide surface coating on the electrode tip member 20 such as a fluorine or hydrogen containing etch gas. The tip electrode member 20 is then subjected to a glow discharge plasma of a hydrocarbon containing gas while being heated, at the same time, to a temperature of approximately 350° C. In this manner, the hydrocarbon is degraded into carbon and hydrogen gas so that the carbon is deposited onto the surface 22 of the electrode tip member 20 and the hydrogen gas enters the surrounding environment.

The deposit carbon may be in the form of a layer or may penetrate and bond with the titanium so as to form a carbon layer, a carbon-titanium layer, a titanium-carbon layer and finally pure titanium (or titanium alloy).

It is to be appreciated that the method of depositing carbon onto the surface 22 of the electrode member 20 as heretofore described can be easily applied to an irregular surface, such as defined by the grooves 28 and the ridges 29 in the distal end 24 of the electrode member 20 of the present invention. The carbon coating results in a low impedance coating on the electrode member 20 which substantially eliminates breakdown of the carbon coating with current reversal. The low impedance further enhances the life of the battery in a cardiac pacer from which the tip electrode member 20 is supplied with current.

It is apparent that one of the advantages of the present invention is that the grooves 28 and the ridges 29 increase the surface area of the distal end 24 of the electrode member 20 to minimize polarization of the tip electrode member 20 and within the enlarged surface area being kept within a small displaced surface area to ensure the sufficient electric current flow to cause muscle depolarization of the organ tissue into which the tip electrode member 20 is implanted.

The irregular grooved surface of the tip electrode member 20 also enhances fixation of the tip electrode member 20 in the trabeculae of the heart.

Further, the number of grooves 28 and ridges 29, as well as the pattern of the grooves 28, comprising grooves 30, 32 and 34, and ridges 29 around the distal end 24 of the electrode tip member 20, can be easily changed and/or controlled when manufacturing the electrode member 20 by merely using a template having other arrangements or configurations of transparent windows therein, such as circular windows which form holes in the tip electrode member.

From the foregoing description, it will be apparent that the tip electrode member 20 of the present invention has a number of advantages, some of which have been described and others of which are inherent in the invention. Also, it will be apparent that modifications can be made to the tip electrode member 20 without departing from the teachings of the present invention.

Accordingly, the scope of the invention is only to be limited as necessitated by the accompanying claims.

We claim:

1. A method for making an implantable tip electrode member for use with a pacing lead, said method including the steps of: forming a tip electrode member from an electrically conductive material, said member having a proximal end and a round-in-cross-section distal end; coating said distal end with a photosensitive material; directing a light source against said distal end through a template having light passage means therein permitting passage of light therethrough, to create a pattern of light-exposed areas and a pattern of non-exposed or dark areas between said light-exposed areas on said distal end, said photosensitive material on said light-exposed areas being polymerized to an insoluble state thereby forming a protective coating on said light-exposed areas; applying a first solvent to said tip electrode member, said first solvent removing said photosensitive material from said non-exposed areas of said tip member thereby leaving a pattern of light-exposed areas having said photosensitive material adhered thereto; applying an etchant to said tip electrode member to etch a plurality of grooves in said non-exposed areas with said light-exposed areas being protected by said photosensitive material to form a plurality of ridges between said grooves; arranging and locating said light passage means so that said plurality of grooves includes a first set of grooves comprising at least two grooves extending circumferentially around said generally round-in-cross-section distal end in generally parallel spaced planes and a second set of grooves comprising at least two grooves extending over said round-in-cross-section distal end in planes perpendicular to the planes of said first set of grooves; and applying a second solvent to said tip electrode member to remove said photosensitive material from said light-exposed areas.

2. The method of claim 1 including the further step of coating said tip member with an electrically conductive material.

3. The method of claim 1 including the step of providing a template which is made of a generally nontransparent material.

4. The method of claim 1 including the step of providing a template in which said light passage means are defined by a plurality of elongate transparent windows.

5. The method of claim 4 wherein said plurality of windows include at least two horizontal elongate first set of windows extending circumferentially around said distal end of said tip electrode member, and being in planes parallel relative to each other, at least two elongate second set of windows extending in planes which are perpendicular to said planes of said first set of windows and being parallel to each other, and at least two elongate third set of windows extending in planes which are perpendicular to said first set of grooves and perpendicular to said second set of grooves and being parallel to each other.

6. The method of claim 4 wherein said plurality of windows includes at least four horizontal elongate first set of windows extending circumferentially around said distal end of said tip electrode member, and being in planes parallel relative to each other, at least four elongate second set of windows extending in planes which are perpendicular to said planes of said first set of windows and being parallel to each other, and at least four elongate third set of windows extending in planes which are perpendicular to said first set of windows and perpendicular to said second set of windows and being parallel to each other.

7. The method of claim 1 including the step of coating said tip member with carbon.

8. The method of claim 1 wherein said step of forming the tip electrode member from electrically conductive material comprises the step of forming the tip electrode member from titanium.

9. The method of claim 1 wherein said step of forming the tip electrode member from electrically conductive material comprises the step of forming the tip electrode member from a titanium alloy.

10. The method of claim 9 wherein said titanium alloy is 90% titanium, 6% aluminum and 4% vanadium.

11. The method of claim 1 wherein said step of coating said distal end with photosensitive material comprises the step of coating said distal end with a photosensitive polymeric material.

12. The method of claim 1 wherein said steps of forming said grooves includes forming grooves which are approximately 0.002 inch deep and approximately 0.002 inch in width.

13. An implantable tip electrode member made of an electrically conductive material and having a proximal end and a generally hemispherically shaped distal end, said generally hemispherically shaped distal end of said tip electrode member having a plurality of grooves in the surface thereof forming a plurality of ridges between said grooves to provide a large surface area within a small displaced surface area, said grooves including a first set of grooves comprising at least two grooves extending circumferentially around said generally hemispherically shaped distal end in generally parallel spaced planes, and a second set of grooves comprising at least two grooves extending over said hemispherically shaped distal end in planes which are perpendicular to the planes of said first set of grooves, thereby to minimize polymerization of the tip electrode member while ensuring sufficient current flow to cause heart muscle depolarization.

14. The tip electrode of claim 13 wherein said grooves are formed by photochemically etching the surface of said generally hemispherically shaped distal end of said tip electrode member.

15. The tip electrode member of claim 13 wherein said first set of grooves include at least four generally parallel grooves extending in a circumferential direction around said tip electrode member and in planes generally normal to an elongate axis of said tip electrode member.

16. The tip electrode member of claim 13 wherein said second set of grooves include at least four elongate grooves extending over said tip electrode member generally perpendicular to the planes of said first set of grooves and said plurality of grooves further including a third set of grooves comprising at least four elongate grooves extending over said tip electrode member perpendicular to the planes of said first and second sets of grooves.

17. The tip electrode member of claim 13 wherein said grooves are approximately 0.002 deep and approximately 0.002 inch wide.

18. The tip electrode member of claim 13 wherein said electrically conductive material from which said tip electrode member is made is titanium.

19. The tip electrode member of claim 13 wherein said tip electrode member is made is a titanium alloy.

20. The tip electrode member of claim 19 wherein said titanium alloy is 90% titanium, 6% aluminum and 4% vanadium.

21. The tip electrode member of claim 13 wherein said tip electrode member has a coating of carbon thereon.

22. The tip electrode member of claim 13 wherein said second set of grooves includes at least two grooves extending over said generally hemispherically shaped distal end in parallel spaced planes which are perpendicular to the planes of said first set of grooves and wherein said plurality of grooves further include a third set of grooves comprising at least two grooves extending over said generally hemispherically shaped distal end in parallel spaced planes which are perpendicular to both the planes of said first set of grooves and to the planes of said second set of grooves.

* * * * *